(12) United States Patent
Epstein et al.

(10) Patent No.: US 7,598,083 B2
(45) Date of Patent: Oct. 6, 2009

(54) CHEMICALLY DEFINED MEDIA COMPOSITIONS

(75) Inventors: David Epstein, Philadelphia, PA (US); Roger Monsell, Willistown, PA (US); Joseph Horwitz, Swarthmore, PA (US); Susan Lenk, Devon, PA (US); Sadettin Ozturk, Paoli, PA (US); Christopher Marsh, Audubon, PA (US)

(73) Assignee: Centocor, Inc., Malvern, PA (US)

( * ) Notice: Subject to any disclaimer, the term of this patent is extended or adjusted under 35 U.S.C. 154(b) by 468 days.

(21) Appl. No.: 11/260,788

(22) Filed: Oct. 27, 2005

(65) Prior Publication Data

US 2006/0094113 A1    May 4, 2006

Related U.S. Application Data

(60) Provisional application No. 60/623,718, filed on Oct. 29, 2004.

(51) Int. Cl.
C12N 5/00 (2006.01)
C12N 5/02 (2006.01)

(52) U.S. Cl. ........................ 435/404; 435/325

(58) Field of Classification Search ........................ None
See application file for complete search history.

(56) References Cited

U.S. PATENT DOCUMENTS

| | | | |
|---|---|---|---|
| 4,282,326 | A | 8/1981 | Moldenhauer et al. |
| 4,533,637 | A | 8/1985 | Yamane et al. |
| 4,657,866 | A | 4/1987 | Kumar et al. |
| 4,767,704 | A | 8/1988 | Cleveland et al. |
| 5,045,468 | A | 9/1991 | Darfler et al. |
| 5,393,668 | A | 2/1995 | Cinatl et al. |
| 6,048,728 | A | 4/2000 | Inlow et al. |
| 6,146,873 | A | 11/2000 | Kistner et al. |
| 6,171,825 | B1 | 1/2001 | Chan et al. |
| 6,358,703 | B1 | 3/2002 | Cho et al. |
| 6,475,725 | B1 | 11/2002 | Reiter et al. |
| 2002/0115152 | A1 | 8/2002 | Cho et al. |
| 2002/0182679 | A1 | 12/2002 | Reiter et al. |
| 2003/0203448 | A1 | 10/2003 | Reiter et al. |

FOREIGN PATENT DOCUMENTS

| EP | 0485689 | 10/2001 |
|---|---|---|
| WO | WO 03/00423 A1 | 1/1993 |
| WO | WO 98/08934 A1 | 3/1998 |
| WO | WO 03/046162 A2 | 6/2003 |

OTHER PUBLICATIONS

Kovár, J and Franěk, F, Serum-free Medium for Hybridoma and Parental Myeloma Cell Cultivation: a Novel Composition of Growth-supporting Substances, *Immunol. Lett.*, vol. 7, (1984), pp. 339-345.
Franěk, F., "Starvation-induced Programmed Death of Hybridoma Cells: Prevention by Amino Acid Mixtures," *Biotechnol. Bioengin.*, vol. 45, (1995), pp. 86-90.
Franěk, F. and Šramková, K. "Cell Suicide in Starving Hybridoma Culture: Survival-signal Effect of Some Amino Acids," *Cytotechnol.*, vol. 23, (1997), pp. 231-239.
Franěk, F. et al., "Plant Protein Hydrolysates: Preparation of Defined Peptide Fractions Promoting Growth and Production in Animal Cell Cultures," *Biotechnol. Prog.*, vol. 16, (2000), pp. 688-692.
Franěk, F. and Chládková-Šramková, K., "Apoptosis and Nutrition: Involvement of Amino Acid Transport System in Repression of Hybridoma Cell Death," *Cytotechnol.*, vol. 18, (1995), pp. 113-117.
Franěk, F. and Dolníková, J., "Hybridoma Growth and Monoclonal Antibody Production in Iron-rich Protein-free Medium: Effect of Nutrient Concentration," *Cytotechnol.*, vol. 7, (1991), pp. 33-38.
Jo, E-C. et al., "Balanced Nutrient Fortification Enables High-density Hybridoma Cell Culture in Batch Culture," *Biotechnol. Bioengin.*, vol. 36, (1990), pp. 717-720.
Franěk, F. and Šramková, K., "Protection of B Lymphocyte Hybridoma against Starvation-induced Apoptosis: Survival-signal role of Some Amino Acids," *Immunol. Lett.*, vol. 52, (1996), pp. 139-144.
Schneider, Y-J., "Optimization of Hybridoma Cell Growth and Monoclonal Antibody Secretion in a Chemically Defined, Serum- and Protein-free Culture Medium," *J. Immunol. Meth.*, vol. 116, (1989), pp. 65-77.
Keen, MJ., and Hale, C., "The Use of Serum-free Medium for the Production of Functionally Active Humanized Monoclonal Antibody from NS/0 Mouse Myeloma Cells Engineered Using Glutamine Synthetase as a Selectable Marker," *Cytotechnol.*, vol. 18, (1996) pp. 207-217.
Qi, YM. et al., "Evaluation of a Simple Protein-free Medium that Supports High Levels of Monoclonal Antibody Production," *Cytotechnol.*, vol. 21, (1996), pp. 95-109.
Franěk, F. and Šramková, K. "Cell Suicide in Starving Hybridoma Culture: Survival-signal Effect of Some Amino Acids," *Cytotechnol.*, vol. 21, (1996), pp. 81-89.
Cleveland, WL. et al., "Routine Large-scale Production of Monoclonal Antibodies in a Protein-free Culture Medium," *J. Immunol. Meth.*, vol. 56, (1983), pp. 221-234.
Chen, Z. et al., "A Low-cost Chemically Defined Protein-free Medium for a Recombinant CHO Cell Line Producing Prothrombin," *Biotechnol. Lett.*, vol. 22, (2000), pp. 837-841.
Tang, X-h. and Shay, NF. "Zinc Has an Insulin-like Effect on Glucose Transport Mediated by Phosphoinositol-3-kinase and Akt in 3T3-L1 Fibroblasts and Adipocytes," *J.Nutrit.*, vol. 131, (2001), pp. 1414-1420.
Ezaki, O. "IIb Group Metal Ions ($Zn^{+2}$, $Cd^{+2}$, and $Hg^{+2}$) Stimulate Glucose Transport Activity by Post-insulin Receptor Kinase Mechanism in Rat Adipocytes," *J.Biol.Chem.* vol. 264, (1989) pp. 16118-16122.
May, JM. And Contoreggi, CS., "The Mechanism of the Insulin-like Effects of Ionic Zinc," *J.Biol.Chem.*, vol. 257, (1982), pp. 4362-4368.

*Primary Examiner*—Lora E Barnhart
(74) *Attorney, Agent, or Firm*—Kirk Baumeister (57) ABSTRACT

Chemically defined media compositions for the culture of eukaryotic cells are disclosed. The compositions are useful for eukaryotic cell culture in perfusion bioreactors and other vessels.

11 Claims, 3 Drawing Sheets

CHEMICALLY DEFINED MEDIA COMPOSITIONS

CROSS REFERENCE TO RELATED APPLICATIONS

This application claims the benefit of U.S. Provisional Application No. 60/623,718, filed 29 Oct. 2004, the entire contents of which is incorporated herein by reference.

FIELD OF THE INVENTION

The present invention relates to chemically defined media compositions for the culture of eukaryotic cells.

BACKGROUND OF THE INVENTION

Contamination of conventional eukaryotic cell culture media with "adventitious particles" such as bacterial, virus or prion particles is a serious potential problem in the industrial preparation of biopharmaceuticals such as antibodies or therapeutic proteins. Such contaminants in a biopharmaceutical are capable of causing patient infections and disease and may limit yields due to increased metabolic burdens on the host productioncell line.

Variant Creutzfeldt-Jakob disease (vCJD) is one example of a patient disease that could be caused by adventitious particle contamination. This disease is prion mediated in humans and is characterized by fatal neurodegeneration. vCJD has been strongly linked with exposure to the Bovine Spongiform Encephalopathy (BSE) prion which causes fatal, neurodegenerative "Mad Cow Disease" in cattle.

Adventitious particle contamination of conventional eukaryotic cell culture media can result from the incorporation of animal-derived components and protein growth factors into conventional media. Such contamination can occur when animal-derived media components are harvested from an animal harboring disease-causing bacteria, viruses, or prions. For example, bovine serum harvested from a cow with BSE may be contaminated with prions capable of causing human vCJD. The ultimate result of such adventitious particle contamination can be the contamination of eukaryotic cell cultures and the biopharmaceuticals prepared from such cultures.

Adventitious particle contamination can be avoided by culturing eukaryotic cells in animal component free cell culture media. Ideally, such media are "chemically defined" such that the media compositions contain only known chemical compounds, and are free of all proteins—even those not of animal origin such as recombinant proteins.

Chemically defined media compositions optimal for production of biopharmaceuticals, such as antibodies, must satisfy several different criteria. First, such compositions must limit eukaryotic cell damage resulting from shear forces and other cell-damaging processes that occur in the bioreactor vessels typically used for biopharmaceutical production. Second, such compositions must enable eukaryotic cell cultures to have high viable cell densities (i.e., number viable cells/ml media) and high percentages of viable cells. Third, such compositions must permit high titers of secreted biopharmaceutical products (i.e., antibody mg/L media) and high specific productivities (i.e., pg antibody/viable cell/day). Lastly, such compositions must limit the production of lactic acid by cultured eukaryotic cells to permit the most efficient cellular use of glucose.

Thus, a need exists for chemically defined media compositions which satisfy these criteria and are optimized for biopharmaceutical production.

SUMMARY OF THE INVENTION

One aspect of the invention is a soluble composition, suitable for producing a cell culture media, wherein the media comprises the following components in the following amounts per liter:

anhydrous $CaCl_2$, 5-200 mg;
anhydrous $MgCl_2$, 15-50 mg;
anhydrous $MgSO_4$, 20-80 mg;
$FeSO_4.7H_2O$, 0.05-0.50 mg;
$Fe(NO_3)_3.9H_2O$, 0.01-0.08 mg;
$ZnSO_4.7H_2O$, 0.40-1.20 mg;
ferric ammonium citrate, 0.04-200 mg;
KCl, 280-500 mg;
NaCl, 5000-7500 mg;
$NaH_2PO_4$—$H_2O$, 30-100 mg;
$Na_2HPO_4$, 30-100 mg;
$CuSO_4.5H_2O$, 0.001-0.005 mg;
$CoCl_2.6H_2O$, 0.001-0.10 mg;
$(NH_4)_6Mo_7O_{24}$ $4H_2O$, 0.001-0.005 mg;
$MnSO_4$—$H_2O$, 0.000070-0.0080 mg;
$NiSO_4.6H_2O$, 0.000025-0.0005 mg;
$Na_2SeO_3$, 0.004-0.07 mg;
$Na_2SiO_3.9H_2O$, 0.02-0.4 mg;
$SnCl_2.2H_2O$, 0.000025-0.0005 mg;
$NH_4VO_3$, 0.0001-0.0025 mg;
D-Glucose, 500-8000 mg;
sodium pyruvate, 0.0-1000 mg;
sodium hypoxanthine, 0.0-20.0 mg;
glycine, 0.0-150 mg;
L-alanine, 0.0-150 mg;
L-arginine.HCl, 200-5000 mg;
L-asparagine.$H_2O$, 40-250 mg;
L-aspartic acid, 20-1000 mg;
L-cysteine.HCl $H_2O$, 25.0-250 mg;
L-cystine.2HCl, 15-150 mg;
L-glutamic acid, 0-1000 mg;
L-histidine.HCl.$H_2O$, 100-500 mg;
L-isoleucine, 50-1000 mg;
L-leucine, 50-1000 mg;
L-lysine.HCl, 100-1000 mg;
L-methionine, 50-500 mg;
L-ornithine.HCl, 0-100 mg;
L-phenylalanine, 25-1000 mg;
L-proline, 0-1000 mg;
L-serine, 50-500 mg;
L-taurine, 0-1000 mg;
L-threonine, 50-600 mg;
L-tryptophan, 2-500 mg;
L-tyrosine.2Na.2$H_2O$, 25-250 mg;
L-valine, 100-1000 mg;
d-biotin, 0.04-1.0 mg;
D-calcium pantothenate, 0.1-5.0 mg;
choline chloride, 1-100 mg;
folic acid, 1-10 mg;
i-Inositol, 10-1000 mg;
nicotinamide, 0.5-30 mg;
p-aminobenzoic acid, 0.1-20 mg;

riboflavin, 0.05-5.0 mg;
thiamine.HCl, 0.5-20 mg;
thymidine, 0-3.0 mg;
vitamin $B_{12}$, 0.05-5.0 mg;
linoleic acid, 0.01-2.0 mg;
DL-α-lipoic acid, 0.03-1.0 mg;
pyridoxine.HCl, 0.5-30 mg;
putrescine.2HCl, 0.025-0.25 mg; and
ethanolamine.HCl, 2-100 mg.

Another aspect of the invention is a soluble composition, suitable for producing a cell culture media, wherein the media comprises the following components in the following amounts per liter:
$CaCl_2$, 100.95 mg;
$MgCl_2$, 24.77 mg;
$MgSO_4$, 42.24 mg;
$FeSO_4.7H_2O$, 0.3607 mg;
$Fe(NO_3)_3.9H_2O$, 0.0432 mg;
$ZnSO_4.7H_2O$, 0.6225 mg;
ferric ammonium citrate, 43.25 mg;
KCl, 386.9 mg;
NaCl, 5866.0 mg;
$NaH_2PO_4$—$H_2O$, 54.07 mg;
$Na_2HPO_4$, 61.44 mg;
$CuSO_4.5H_2O$, 0.003287 mg;
$CoCl_2.6H_2O$, 0.0020606 mg;
$(NH_4)_6Mo_7O_{24}.4H_2O$, 0.000535 mg;
$MnSO_4.H_2O$, 0.00008571 mg;
$NiSO_4.6H_2O$, 0.0000514 mg;
$Na_2SeO_3$, 0.007489 mg;
$Na_2SiO_3.9H_2O$, 0.03671 mg;
$SnCl_2.2H_2O$, 0.0000488 mg;
$NH_4VO_3$, 0.0002530 mg;
D-Glucose, 3680.52 mg;
sodium pyruvate, 100 mg;
sodium hypoxanthine, 2.069 mg;
glycine, 16.23 mg;
L-alanine, 79.31 mg;
L-arginine.HCl, 674.89 mg;
L-asparagine.$H_2O$, 182.25 mg;
L-aspartic acid, 67.23 mg;
L-cysteine.HCl.$H_2O$, 57.63 mg;
L-cystine.2HCl, 106.70 mg;
L-glutamic acid, 6.36 mg;
L-histidine.HCl.$H_2O$, 250.55 mg;
L-isoleucine, 245.43 mg;
L-leucine, 263.42 mg;
L-lysine.HCl, 276.41 mg;
L-methionine, 85.40 mg;
L-ornithine.HCl, 2.44 mg;
L-phenylalanine, 104.23 mg;
L-proline, 14.94 mg;
L-serine, 146.36 mg;
L-taurine, 3.64 mg;
L-threonine, 199.09 mg;
L-tryptophan, 70.71 mg;
L-tyrosine.2Na.2$H_2O$, 195.58 mg;
L-valine, 174.34 mg;
d-biotin, 0.4359 mg;
D-calcium pantothenate, 1.9394 mg;
choline chloride, 10.8009 mg;
folic acid, 3.4329 mg;
i-inositol, 81.7965 mg;
nicotinamide, 3.1342 mg;
p-aminobenzoic acid, 2.1645 mg;
riboflavin, 0.5359 mg;
thiamine.HCl, 2.3377 mg;
thymidine, 0.316 mg;
vitamin $B_{12}$, 0.5887 mg;
linoleic acid, 0.0364 mg;
DL-α-lipoic acid, 0.0909 mg;
pyridoxine.HCl, 3.0442 mg;
putrescine.2HCl, 0.0701 mg; and
ethanolamine.HCl, 14.37 mg.

The invention also provides compositions comprising cell culture media which can be made from the soluble compositions of the invention.

DETAILED DESCRIPTION OF THE INVENTION

All publications, including but not limited to patents and patent applications, cited in this specification are herein incorporated by reference as though fully set forth.

The term "buffering molecule" as used herein and in the claims means a molecule that has a buffering range suitable for maintaining a pH between 5.9 and 7.8.

The term "$pK_a$" as used herein and in the claims means the negative logarithm of the acid dissociation constant ($K_a$) of a buffering molecule in an aqueous solution. $pK_a$ is, in part, a function of the temperature of the aqueous solution in which a buffering molecule is solubilized.

The term "cell protectant" as used herein and in the claims means a substance that protects eukaryotic cells from damage. Such damage may be caused, for example, by shear forces or the effects of gas bubble sparging in a bioreactor vessel.

The present invention provides chemically defined compositions useful in the culture of eukaryotic cells. Such eukaryotic cells may have insect, avian, mammalian, or other origins. These cells may secrete a protein, such as an antibody, or produce other useful products or results. These proteins, products, or results may be constitutively produced by a cell or produced as the result of transfection with a nucleic acid sequence. The cells may be cultured in liquid media as suspension cultures or as adherent cultures. Cells may also be cultured by suspension in semi-solid media comprising the compositions of the invention.

Cells may be cultured in a variety of vessels including, for example, perfusion bioreactors, cell bags, culture plates, flasks and other vessels well known to those of ordinary skill in the art. Ambient conditions suitable for cell culture, such as temperature and atmospheric composition, are also well known to those skilled in the art. Methods for the culture of cells are also well known to those skilled in the art.

The compositions of the invention are particularly useful in the culture of mammalian cells. Examples of mammalian cells include myeloma derived cells, non-immortalized cells of the B cell lineage, and immortalized cells of the B cell lineage such as hybridomas. Examples of myeloma derived cell lines include the SP2/0 (American Type Culture Collection (ATCC), Manasas, Va., CRL-1581), NS0 (European Collection of Cell Cultures (ECACC), Salisbury, Wiltshire, UK, ECACC No. 85110503), FO (ATCC CRL-1646), and Ag653 (ATCC CRL-1580) cell lines which were obtained from mice. The C743B cell line is an example of a SP2/0 derived cell line that produces a fully human, anti-IL-12 mAb as the result of stable transfection. The YB2/0 cell line (ATCC CRL-1662) is an example of a myeloma derived cell line obtained from rats (*Rattus norvegicus*). An example of a myeloma derived cell line obtained from humans is the U266 cell line (ATTC CRL-TIB-196). Some myeloma derived cell lines, such as NS0, YB2/0, and Ag653 cells and related cell lines may require chemically defined lipid concentrates or other supplements for successful culture. Those skilled in the art will recognize other myeloma cell lines and myeloma derived cell lines as well as any supplements required for the successful culture of such cells.

In one aspect the invention provides a soluble composition, suitable for producing a cell culture media, wherein the media comprises the following components in the following amounts per liter:
anhydrous $CaCl_2$, 5-200 mg;
anhydrous $MgCl_2$, 15-50 mg;
anhydrous $MgSO_4$, 20-80 mg;
$FeSO_4.7H_2O$, 0.05-0.50 mg;
$Fe(NO_3)_3.9H_2O$, 0.01-0.08 mg;
$ZnSO_4.7H_2O$, 0.40-1.20 mg;
ferric ammonium citrate, 0.04-200 mg;
KCl, 280-500 mg;
NaCl, 5000-7500 mg;
$NaH_2PO_4.H_2O$, 30-100 mg;
$Na_2HPO_4$, 30-100 mg;
$CuSO_4.5H_2O$, 0.001-0.005 mg;
$CoCl_2.6H_2O$, 0.001-0.10 mg;
$(NH_4)_6Mo_7O_{24} 4H_2O$, 0.001-0.005 mg;
$MnSO_4.H_2O$, 0.000070-0.0080 mg;
$NiSO_4.6H_2O$, 0.000025-0.0005 mg;
$Na_2SeO_3$, 0.004-0.07 mg;
$Na_2SiO_3.9H_2O$, 0.02-0.4 mg;
$SnCl_2.2H_2O$, 0.000025-0.0005 mg;
$NH_4VO_3$, 0.0001-0.0025 mg;
D-Glucose, 500-8000 mg;
sodium pyruvate, 0.0-1000 mg;
sodium hypoxanthine, 0.0-20.0 mg;
glycine, 0.0-150 mg;
L-alanine, 0.0-150 mg;
L-arginine.HCl, 200-5000 mg;
L-asparagine.$H_2O$, 40-250 mg;
L-aspartic acid, 20-1000 mg;
L-cysteine.HCl $H_2O$, 25.0-250 mg;
L-cystine.2HCl, 15-150 mg;
L-glutamic acid, 0-1000 mg;
L-histidine.HCl.$H_2O$, 100-500 mg;
L-isoleucine, 50-1000 mg;
L-leucine, 50-1000 mg;
L-lysine.HCl, 100-1000 mg;
L-methionine, 50-500 mg;
L-ornithine.HCl, 0-100 mg;
L-phenylalanine, 25-1000 mg;
L-proline, 0-1000 mg;
L-serine, 50-500 mg;
L-taurine, 0-1000 mg;
L-threonine, 50-600 mg;
L-tryptophan, 2-500 mg;
L-tyrosine-2Na-2$H_2O$, 25-250 mg;
L-valine, 100-1000 mg;
d-biotin, 0.04-1.0 mg;
D-calcium pantothenate, 0.1-5.0 mg; choline chloride, 1-100 mg;
folic acid, 1-10 mg;
i-Inositol, 10-1000 mg;
nicotinamide, 0.5-30 mg;
p-aminobenzoic acid, 0.1-20 mg;
riboflavin, 0.05-5.0 mg;
thiamine.HCl, 0.5-20 mg;
thymidine, 0-3.0 mg;
vitamin $B_{12}$, 0.05-5.0 mg;
linoleic acid, 0.01-2.0 mg;
DL-α-lipoic acid, 0.03-1.0 mg;
pyridoxine.HCl, 0.5-30 mg;
putrescine.2HCl, 0.025-0.25 mg; and
ethanolamine.HCl, 2-100 mg.

This type of soluble composition has been named "MET" and typically is a powder.

In another aspect the invention provides a soluble composition, suitable for producing a cell culture media, wherein the media comprises the following components in the following amounts per liter:
$CaCl_2$, 100.95 mg;
$MgCl_2$, 24.77 mg;
$MgSO_4$, 42.24 mg;
$FeSO_4.7H_2O$, 0.3607 mg;
$Fe(NO_3)_3.9H_2O$, 0.0432 mg;
$ZnSO_4.7H_2O$, 0.6225 mg;
ferric ammonium citrate, 43.25 mg;
KCl, 386.9 mg;
NaCl, 5866.0 mg;
$NaH_2PO_4.H_2O$, 54.07 mg;
$Na_2HPO_4$, 61.44 mg;
$CuSO_4.5H_2O$, 0.003287 mg;
$CoCl_2.6H_2O$, 0.0020606 mg;
$(NH_4)_6Mo_7O_{24}.4H_2O$, 0.000535 mg;
$MnSO_4.H_2O$, 0.00008571 mg;
$NiSO_4.6H_2O$, 0.0000514 mg;
$Na_2SeO_3$, 0.007489 mg;
$Na_2SiO_3.9H_2O$, 0.03671 mg;
$SnCl_2.2H_2O$, 0.0000488 mg;
$NH_4VO_3$, 0.0002530 mg;
D-Glucose, 3680.52 mg;
sodium pyruvate, 100 mg;
sodium hypoxanthine, 2.069 mg;
glycine, 16.23 mg;
L-alanine, 79.31 mg;
L-arginine.HCl, 674.89 mg;
L-asparagine.$H_2O$, 182.25 mg;
L-aspartic acid, 67.23 mg;
L-cysteine.HCl.$H_2O$, 57.63 mg;
L-cystine.2HCl, 106.70 mg;
L-glutamic acid, 6.36 mg;
L-histidine.HCl.$H_2O$, 250.55 mg;
L-isoleucine, 245.43 mg;
L-leucine, 263.42 mg;
L-lysine-HCl, 276.41 mg;
L-methionine, 85.40 mg;
L-ornithine-HCl, 2.44 mg;
L-phenylalanine, 104.23 mg;
L-proline, 14.94 mg;
L-serine, 146.36 mg;
L-taurine, 3.64 mg;
L-threonine, 199.09 mg;
L-tryptophan, 70.71 mg;
L-tyrosine.2Na.2$H_2O$, 195.58 mg;
L-valine, 174.34 mg;
d-biotin, 0.4359 mg;
D-calcium pantothenate, 1.9394 mg;
choline chloride, 10.8009 mg;
folic acid, 3.4329 mg;
i-inositol, 81.7965 mg;
nicotinamide, 3.1342 mg;
p-aminobenzoic acid, 2.1645 mg;
riboflavin, 0.5359 mg;
thiamine.HCl, 2.3377 mg;
thymidine, 0.316 mg;
vitamin $B_{12}$, 0.5887 mg;
linoleic acid, 0.0364 mg;
DL-α-lipoic acid, 0.0909 mg;

pyridoxine.HCl, 3.0442 mg;
putrescine.2HCl, 0.0701 mg; and
ethanolamine.HCl, 14.37 mg.

This soluble composition has been named "MET 1.5" and typically is a powder.

In one embodiment the soluble MET and MET 1.5 compositions of the invention comprise a buffering molecule with a $pK_a$ of between 5.9 and 7.8; and a cell protectant. Examples of buffering molecules with a $pK_a$ of between 5.9 and 7.8 include MOPS ($pK_a$ 7.20 at 25° C.; $pK_a$ 7.02 at 37° C.), TES (2-[tris (hydroxymothyl) methyl]amino ethanesulphonic acid; $pK_a$ 7.40 at 25° C.; $pK_a$ 7.16 at 37° C.), and imidazole ($pK_a$ 6.95 at 25° C.). Examples of cell protectants are non-ionic surfactants such as Pluronic-F68, polyvinyl alcohol (PVA), polyethylene glycol (PEG), and dextran sulfate. Those skilled in the art will recognize other buffering molecules with a $pK_a$ of between 5.9 and 7.8 and cell protectants.

In another embodiment of the soluble MET compositions of the invention the buffering molecule consists of MOPS in the amount of 1047-5230 mg per liter of media volume, and the cell protectant consists of Pluronic-F68 in the amount of 250-1500 mg per liter of media volume.

In another embodiment of the soluble MET1.5 compositions of the invention the buffering molecule consists of MOPS in the amount of 2709.66 mg per liter of media volume, and the cell protectant consists of Pluronic-F68 in the amount of 865.80 mg per liter of media volume.

The soluble compositions of the invention may be prepared in a variety of forms. It is preferred that the soluble compositions of the invention are prepared in the form of a powder. The powdered forms of the soluble compositions of the invention are suitable for cell culture for at least 3 years from the date the soluble composition is prepared. The soluble compositions of the invention may also be prepared, for example, in the form of one or more pellets or tablets.

The soluble compositions of the invention can be solubilized in water. Typically, the water used to solubilize the soluble compositions of the invention has a resistivity of 18.2 MΩ·cm at 25° C., a total organic content of less than 20 ppb, a total microorganism content of less than 10 colony forming units per ml, a total heavy metal content of less than 0.01 ppm, a total silicates content of less than 0.01 ppb, and a total dissolved solids content of less than 0.03 ppm. Water with these properties can be prepared using a Super-Q™ Plus Water Purification System (Millipore Corp., Billerica, Mass., USA). The water used to solubilize the soluble compositions of the invention may also be filtered through a filter suitable for the removal of microorganisms. A filter with a 0.22 μM pore size is an example of such a filter. Microorganisms and other adventitious particles may also be removed or inactivated by other means well known in the art.

In one embodiment the invention provides a composition comprising a cell culture media made by the steps comprising selecting a final media volume, providing a soluble MET composition, solubilizing the soluble composition in a volume of water less than the final media volume, adding 1.022 g of L-glutamine per liter of final media volume, adding a bicarbonate ion providing substance sufficient to a produce a bicarbonate ion concentration of between 0.020 M and 0.030 M in the final media volume, optionally adding at least one substance selected from the group consisting of mycophenolic acid, hypoxanthine, xanthine, or soy hydrosylate, adding a quantity of base sufficient to adjust the pH of the solution to between pH 5.9 and pH 7.8, and adding water sufficient to bring the volume of the composition to the selected final media volume. In this embodiment of the invention the media composition that is the product of this process has been named "MET media." Typically MET media is a liquid media.

In another embodiment the invention provides a composition comprising a cell culture media made by the steps comprising selecting a final media volume; providing a soluble MET1.5 composition, solubilizing the soluble composition in a volume of water less than the final media volume, adding 1.022 g of L-glutamine per liter of final media volume, adding a bicarbonate ion providing substance sufficient to a produce a bicarbonate ion concentration of between 0.020 M and 0.030 M in the final media volume, optionally adding at least one substance selected from the group consisting of mycophenolic acid, hypoxanthine, xanthine or soy hydrosylate, adding a quantity of base sufficient to adjust the pH of the solution to between pH 5.9 and pH 7.8, and adding water sufficient to bring the volume of the composition to the selected final media volume. In this embodiment of the invention the media composition that is the product of this process has been named "MET 1.5 media." Typically MET 1.5 media is a liquid media.

In one embodiment of the invention the bicarbonate ion providing substance sufficient to a produce a bicarbonate ion concentration of between 0.020 M and 0.030 M in the final media volume is 2.1 g of $NaHCO_3$ per liter of final media volume. Adding this amount of $NaHCO_3$ per liter of final media volume produces a bicarbonate ion concentration of 0.025 M in the final media volume.

In one embodiment of the invention MET 1.5 media comprises the following components added in the following amounts per liter:
0.5 mg mycophenolic acid;
2.5 mg hypoxanthine; and
50 mg xanthine.

The MET media and MET 1.5 media compositions of the invention are typically provided to cells as a liquid media. The pH of the MET media and MET 1.5 media compositions of the invention is between pH 5.9 and pH 7.8. The pH of a liquid is a function of the temperature of the liquid. It is preferred that the pH of each media composition be between 7.1 and 7.25 at the temperature at which eukaryotic cell culture is being performed. Eukaryotic cell culture may be performed at temperatures higher or lower than 37° C., but is typically performed at 37° C.

In some applications liquid MET media and liquid MET 1.5 media may be used in the preparation of semi-solid cell culture media. For example, methylcellulose may be used to generate a semi-solid media incorporating the liquid MET media and liquid MET 1.5 media compositions of the invention. Such semi-solid media may be prepared by methods well known to those skilled in the art. Eukaryotic cells may be suspended in such semi-solid media and cultured by methods well known to those skilled in the art.

Other substances that can enhance cell growth or productivity may also be added to the soluble MET, MET media, soluble MET 1.5 and MET 1.5 media compositions of the invention. These substances may be lipids, nucleosides, peptide chains, corticosteroids, steroids, and the like. Such substance may be, for example:
adenosine preferably 0-20 μM;
guanosine preferably 0-20 μM;
cytidine preferably 0-20 μM;
uridine preferably 0-20 μM;
deoxyadenosine preferably 0-20 μM;
deoxyguanosine preferably 0-20 μM;
deoxycytidine preferably 0-20 μM;
thymidine preferably 0-20 μM;

dexamethasone preferably 10-150 nM;
hydrocortisone preferably 0-150 μM;
L-glycine-L-Lysine-L-glycine (GKG) peptide chain preferably 0-200 μm;
N-acetyl cysteine preferably 0-500 mg/L;
betaine preferably 0-500 mg/L;
L-malic acid preferably 0-500 mg/L;
oxaloacetic acid preferably 0-500 mg/L;
glycyrrhizic acid preferably 0-500 mg/L;
glycyrrhizic acid ammonium salt preferably 0-500 mg/L;
α-ketoglutarate preferably 0-500 mg/L;
L-leucine preferably 245-490 mg/L;
L-isoleucine preferably 220-440 mg/L;
L-lysine-HCl preferably 187-360 mg/L;
L-valine preferably 155-310 mg/L;
L-methionine preferably 57-114 mg/L;
L-phenylalanine preferably 76-152 mg/L;
L-serine preferably 37-74 mg/L;
L-threonine preferably 107-214 mg/L;
L-arginine.HCl preferably 200-300 mg/L;
L-asparagine preferably 114-170 mg/L;
L-aspartic acid (10-25 mg/L);
L-cysteine.HCl.H$_2$O preferably 46-75 mg/L;
Histidine.HCl.H$_2$O preferably 75-150 mg/L;
L-tyrosine preferably 40-80 mg/L;
L-tryptophan preferably 41-82 mg/L;
nicotinamide preferably 0.9-1.8 mg/L; and
ethanolamine HCl preferably 14-20 mg/L.

The quantities of each substance added to the compositions of the invention are those necessary to achieve the preferred molar concentration or mass per unit media volume prepared shown above.

The present invention is further described with reference to the following examples. These examples are merely to illustrate various aspects of the present invention and are not intended as limitations of this invention.

EXAMPLE 1

Eukaryotic Cell Viability in MET 1.5 Cell Culture Media

Figure 1:
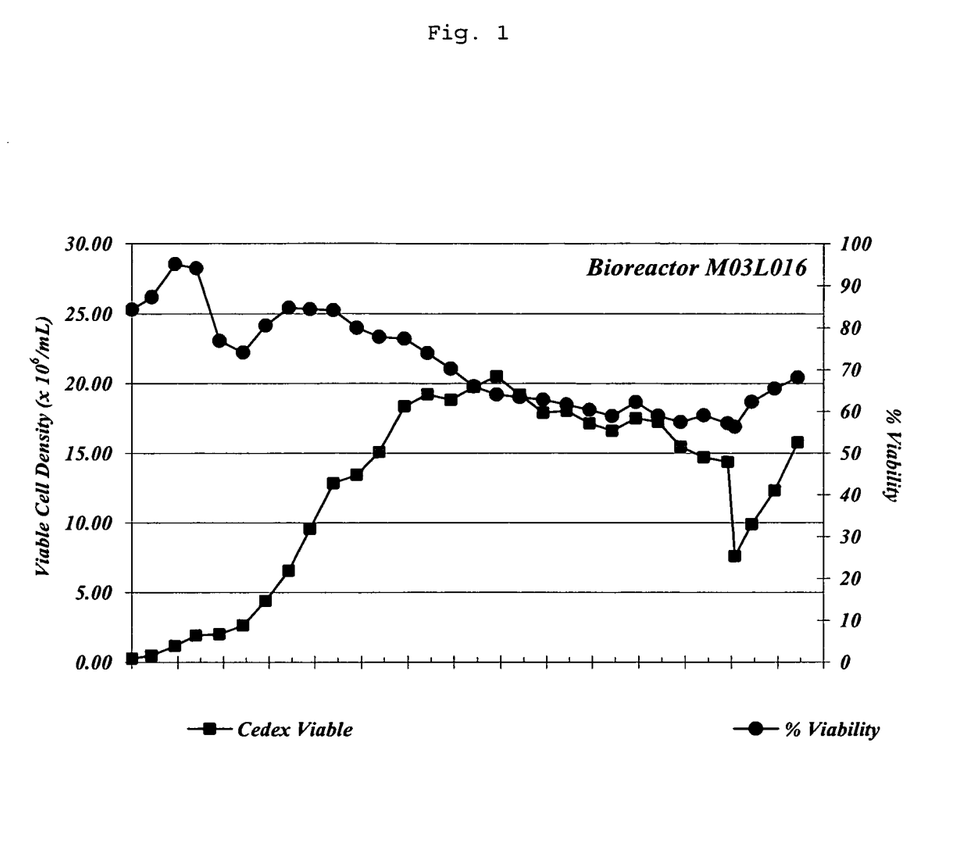
FIG. 1. Eukaryotic cell viability in MET 1.5 cell culture media.

Chemically defined MET 1.5 cell culture media can sustain high cell growth and viability (FIG. 1). To examine viable cell numbers, MET 1.5 media was supplied to 3 L perfusion bioreactors. Bioreactors were then inoculated with C743B cells such that the initial cell density was 3×10$^6$ cells/ml of MET 1.5 media. The C743B cell line produces a fully human, anti-IL-12 mAb and is a chemically adapted cell line derived from SP2/0 myeloma cells. C743B cells were grown for 29 days in the bioreactor and viable cell densities were monitored. Cell culture media was neutralized with a 0.2 M Na$_2$CO$_3$ (aq) solution for the first 9 days of culture and with 0.2 M Na$_2$CO$_3$, 0.0054 M K$_2$CO$_3$ (aq). Excessive cell density in the bioreactor was prevented by the removed of biomass from the bioreactor; cell removal began on day 15 and was gradually increased until day 26. The bioreactor was perfused with one volume of MET 1.5 media per day. Viable cell numbers were determined via a standard trypan blue dye exclusion assay using a CEDEX cell counter (Innovatis AG, Bielefeld, Del.). Total cell numbers for calculation of the percentage of viable cells were determined with the CEDEX instrument. For each determination the CEDEX instrument was used according to the manufacturer's instructions. O$_2$ and CO$_2$ were supplied to the bioreactor as a gas stream sparged into the bioreactor vessel. Data presented in Example 1, 2, and 3 are all from the same bioreactor run.

EXAMPLE 2

Antibody Titer and Specific Productivity in MET 1.5 Cell Culture Media

Figure 2:
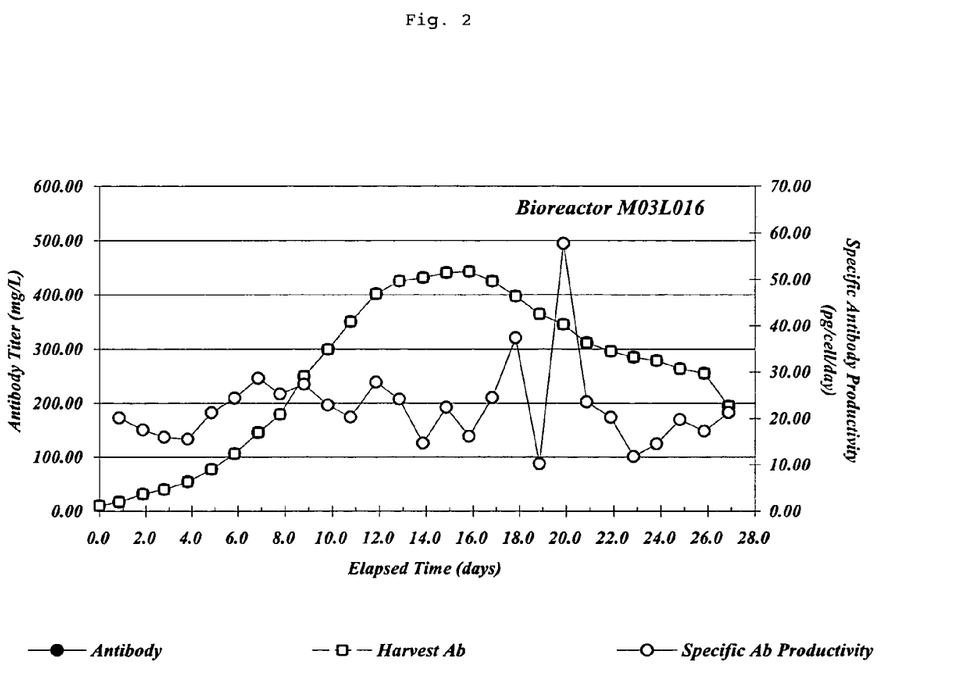
FIG. 2. Antibody titer and specific productivity in MET 1.5 cell culture media.

Chemically defined MET 1.5 cell culture media can sustain high monoclonal antibody titers and specific productivity (FIG. 2). Cell culture and bioreactor operation was as described above. Fully human, anti-IL-12 mAb titers (mg/L) were determined by standard nephelometry techniques using a Beckman Array Analyzer. A purified fully human, anti-IL-12 mAb of known concentration was used to generate a standard curve for the determination of mAb titers by nephelometry. Viable cell numbers for calculation of specific productivity were determined as described above. Data presented in Example 1, 2, and 3 are all from the same bioreactor run.

EXAMPLE 3

Decreased Lactate Production in MET 1.5 Cell Culture Media

Lactate concentrations in MET 1.5 media decrease (FIG. 3) as viable cell density increases (FIG. 1). Cell culture and bioreactor operation was as described above. Lactate concentrations and glucose concentrations in the bioreactor culture media were determined using standard assays. Data presented in Example 1, 2, and 3 are all from the same bioreactor run.

Figure 3:
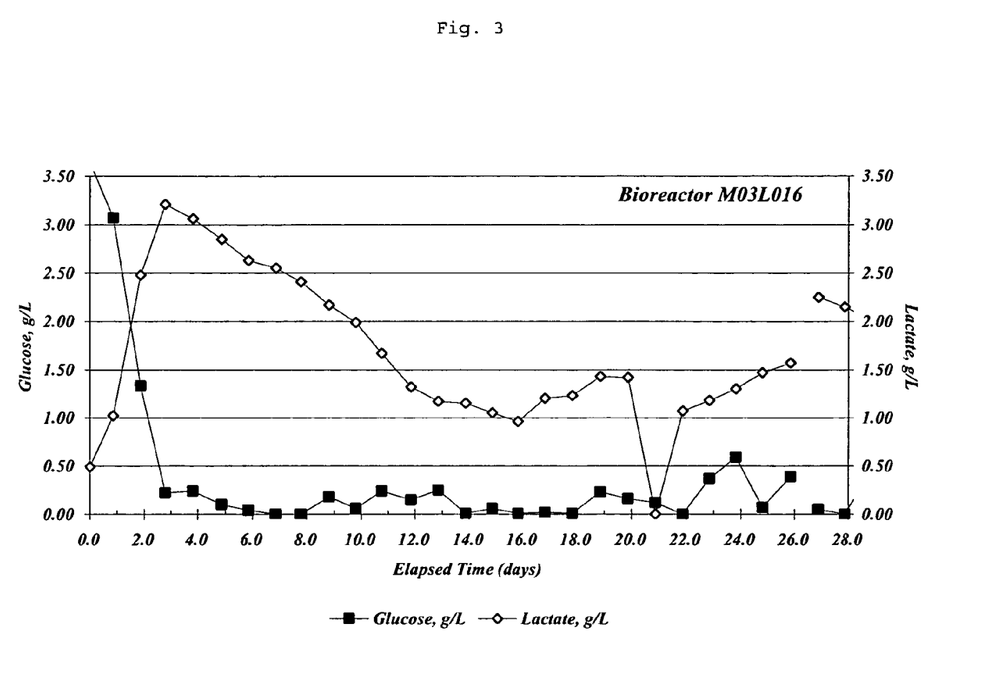
FIG. 3. Decreased lactate production in MET 1.5 cell culture media.

As FIG. 3 indicates, lactate concentrations in MET 1.5 media gradually decreased until day 16 when biomass removal to decrease total cell density in the bioreactor began. During the same period glucose concentrations remained comparatively constant (FIG. 3). Comparison of FIG. 3 to FIG. 1 reveals that viable C743B cell numbers in the same bioreactor were increasing until day 16. Together this data indicates a decrease in lactate production by C743B cells cultured in MET 1.5 media and more efficient metabolism of D-glucose by cells cultured in MET 1.5 media.

The present invention now being fully described, it will be apparent to one of ordinary skill in the art that many changes and modifications can be made thereto without departing from the spirit or scope of the appended claims.

The invention claimed is:

1. A soluble composition, suitable for producing a final volume of cell culture media, wherein the composition comprises the following components in the following amounts per liter of the final volume of cell culture media:
anhydrous CaCl$_2$, 5-200 mg;
anhydrous MgCl$_2$, 15-50 mg;
anhydrous MgSO$_4$, 20-80 mg;
FeSO$_4$.7H$_2$O, 0.05-0.50 mg;
Fe(NO$_3$)$_3$.9H$_2$O, 0.01-0.08 mg;
ZnSO$_4$.7H$_2$O, 0.40-1.20 mg;
ferric ammonium citrate, 0.04-200 mg;
KCl, 280-500 mg;
NaCl, 5000-7500 mg;
NaH$_2$PO$_4$.H$_2$O, 30-100 mg;
Na$_2$HPO$_4$, 30-100 mg;
CuSO$_4$.5H$_2$O, 0.001-0.005 mg;
CoCl$_2$.6H$_2$O, 0.001-0.10 mg;
(NH$_4$)$_6$Mo$_7$O$_{24}$ 4H$_2$O, 0.001-0.005 mg;
MnSO$_4$.H$_2$O, 0.000070-0.0080 mg;

$NiSO_4.6H_2O$, 0.000025-0.0005 mg;
$Na_2SeO_3$, 0.004-0.07 mg;
$Na_2SiO_3.9H_2O$, 0.02-0.4 mg;
$SnCl_2.2H_2O$, 0.000025-0.0005 mg;
$NH_4VO_3$, 0.0001-0.0025 mg;
D-Glucose, 500-8000 mg;
sodium pyruvate, 0.0-1000 mg;
sodium hypoxanthine, 0.0-20.0 mg;
glycine, 0.0-150 mg;
L-alanine, 0.0-150 mg;
L-arginine.HCl, 200-5000 mg;
L-asparagine.$H_2O$, 40-250 mg;
L-aspartic acid, 20-1000 mg;
L-cysteine.HCl $H_2O$, 25.0-250 mg;
L-cystine.2HCl, 15-150 mg;
L-glutamic acid, 0-1000 mg;
L-histidine.HCl.$H_2O$, 100-500 mg;
L-isoleucine, 50-1000 mg;
L-leucine, 50-1000 mg;
L-lysine.HCl, 100-1000 mg;
L-methionine, 50-500 mg;
L-ornithine.HCl, 0-100 mg;
L-phenylalanine, 25-1000 mg;
L-proline, 0-1000 mg;
L-serine, 50-500 mg;
L-taurine, 0-1000 mg;
L-threonine, 50-600 mg;
L-tryptophan, 2-500 mg;
L-tyrosine.2Na.2$H_2O$, 25-250 mg;
L-valine, 100-1000 mg;
d-biotin, 0.04-1.0 mg;
D-calcium pantothenate, 0.1-5.0 mg;
choline chloride, 1-100 mg;
folic acid, 1-10 mg;
i-Inositol, 10-1000 mg;
nicotinamide, 0.5-30 mg;
p-aminobenzoic acid, 0.1-20 mg;
riboflavin, 0.05-5.0 mg;
thiamine.HCl, 0.5-20 mg;
thymidine, 0-3.0 mg;
vitamin $B_{12}$, 0.05-5.0 mg;
linoleic acid, 0.01-2.0 mg;
DL-α-lipoic acid, 0.03-1.0 mg;
pyridoxine.HCl, 0.5-30 mg;
putrescine.2HCl, 0.025-0.25 mg; and
ethanolamine.HCl, 2-100 mg.

2. The soluble composition of claim 1 further comprising a buffering molecule with a $pK_a$ between 5.9 and 7.8 and a cell protectant.

3. The soluble composition of claim 2 wherein the buffering molecule consists of MOPS in the amount of 1047-5230 mg per liter of final media volume and the cell protectant consists of Pluronic-F68 in the amount of 250-1500 mg per liter of final media volume.

4. A composition comprising a cell culture media made by the steps comprising:
    a) selecting a final media volume;
    b) providing the soluble composition of claim 2 or claim 3;
    c) solubilizing the soluble composition in a volume of water less than the final media volume;
    d) adding 1.022 g of L-glutamine per liter of final media volume;
    e) adding a bicarbonate ion providing substance sufficient to produce a bicarbonate ion concentration of between 0.020 M and 0.030 M in the final media volume;
    f) optionally adding at least one substance selected from the group consisting of mycophenolic acid, hypoxanthine, xanthine, and soy hydrolysate;
    g) adding a quantity of base sufficient to adjust the pH of the solution to between pH 5.9 and pH 7.8; and
    h) adding water sufficient to bring the volume of the composition to the selected final media volume.

5. The composition of claim 4 where the bicarbonate ion providing substance sufficient to a produce a bicarbonate ion concentration of between 0.020 M and 0.030 M in the final media volume is 2.1 g of $NaHCO_3$ per liter of final media volume.

6. A soluble composition, suitable for producing a final volume of cell culture media, wherein the composition comprises the following components in the following amounts per liter of the final volume of cell culture media:
$CaCl_2$, 100.95 mg;
$MgCl_2$, 24.77 mg;
$MgSO_4$, 42.24 mg;
$FeSO_4.7H_2O$, 0.3607 mg;
$Fe(NO_3)_3.9H_2O$, 0.0432 mg;
$ZnSO_4.7H_2O$, 0.6225 mg;
ferric ammonium citrate, 43.25 mg;
KCl, 386.9 mg;
NaCl, 5866.0 mg;
$NaH_2PO_4.H_2O$, 54.07 mg;
$Na_2HPO_4$, 61.44 mg;
$CuSO_4.5H_2O$, 0.003287 mg;
$CoCl_2.6H_2O$, 0.0020606 mg;
$(NH_4)_6Mo_7O_{24}.4H_2O$, 0.000535 mg;
$MnSO_4.H_2O$, 0.00008571 mg;
$NiSO_4.6H_2O$, 0.0000514 mg;
$Na_2SeO_3$, 0.007489 mg;
$Na_2SiO_3.9H_2O$, 0.03671 mg;
$SnCl_2.2H_2O$, 0.0000488 mg;
$NH_4VO_3$, 0.0002530 mg;
D-Glucose, 3680.52 mg;
sodium pyruvate, 100 mg;
sodium hypoxanthine, 2.069 mg;
glycine, 16.23 mg;
L-alanine, 79.31 mg;
L-arginine.HCl, 674.89 mg;
L-asparagine.$H_2O$, 182.25 mg;
L-aspartic acid, 67.23 mg;
L-cysteine.HCl.$H_2O$, 57.63 mg;
L-cystine.2HCl, 106.70 mg;
L-glutamic acid, 6.36 mg;
L-histidine.HCl.$H_2O$, 250.55 mg;
L-isoleucine, 245.43 mg;
L-leucine, 263.42 mg;
L-lysine.HCl, 276.41 mg;
L-methionine, 85.40 mg;
L-ornithine.HCl, 2.44 mg;
L-phenylalanine, 104.23 mg;
L-proline, 14.94 mg;
L-serine, 146.36 mg;
L-taurine, 3.64 mg;
L-threonine, 199.09 mg;
L-tryptophan, 70.71 mg;
L-tyrosine.2Na.2$H_2O$, 195.58 mg;
L-valine, 174.34 mg;
d-biotin, 0.4359 mg;
D-calcium pantothenate, 1.9394 mg;
choline chloride, 10.8009 mg;
folic acid, 3.4329 mg;
i-inositol, 81.7965 mg;
nicotinamide, 3.1342 mg;

p-aminobenzoic acid, 2.1645 mg;
riboflavin, 0.5359 mg;
thiamine.HCl, 2.3377 mg;
thymidine, 0.316 mg;
vitamin $B_{12}$, 0.5887 mg;
linoleic acid, 0.0364 mg;
DL-α-lipoic acid, 0.0909 mg;
pyridoxine.HCl, 3.0442 mg;
putrescine.2HCl, 0.0701 mg; and
ethanolamine.HCl, 14.37 mg.

7. The soluble composition of claim 6 further comprising a buffering molecule with a $pK_a$ of between 5.9 and 7.8 and a cell protectant.

8. The soluble composition of claim 7 wherein the buffering molecule consists of MOPS in the amount of 2709.66 mg per liter of final media volume, and the cell protectant consists of Pluronic-F68 in the amount of 865.80 mg per liter of final media volume.

9. The soluble composition of claim 7 further comprising the following components in the following amounts per liter of final media volume:
0.5 mg mycophenolic acid;
2.5 mg hypoxanthine; and
50 mg xanthine.

10. A composition comprising a cell culture media made by the steps comprising:
 a) selecting a final media volume;
 b) providing the soluble composition of claim 7 or claim 8;
 c) solubilizing the soluble composition in a volume of water less than the final media volume;
 d) adding 1.022 g of L-glutamine per liter of final media volume;
 e) adding a bicarbonate ion providing substance sufficient to produce a bicarbonate ion concentration of between 0.020 M and 0.030 M in the final media volume;
 f) optionally adding at least one substance selected from the group consisting of mycophenolic acid, hypoxanthine, xanthine and soy hydrolysate;
 g) adding a quantity of base sufficient to adjust the pH of the solution to between pH 5.9 and pH 7.8; and
 h) adding water sufficient to bring the volume of the composition to the selected final media volume.

11. The composition of claim 10 where the bicarbonate ion providing substance sufficient to a produce a bicarbonate ion concentration of between 0.020 M and 0.030 M in the final media volume is 2.1 g of $NaHCO_3$ per liter of final media volume.

* * * * *